United States Patent [19]

Wun

[11] Patent Number: 5,073,626

[45] Date of Patent: Dec. 17, 1991

[54] AFFINITY PURIFICATION OF PLASMINOGEN ACTIVATOR INHIBITOR I USING A MODIFIED UROKINASE

[75] Inventor: Tze-Chein Wun, St. Louis, Mo.

[73] Assignee: Monsanto Company, St. Louis, Mo.

[21] Appl. No.: 532,410

[22] Filed: Jun. 4, 1990

Related U.S. Application Data

[63] Continuation-in-part of Ser. No. 268,916, Nov. 9, 1988, abandoned.

[51] Int. Cl.$^5$ .......................... C07K 3/18; C07K 15/06
[52] U.S. Cl. .................................... 530/350; 530/413; 435/69.2; 435/212; 435/215
[58] Field of Search .................. 530/412, 413, 350; 435/69.2, 212, 215

[56] References Cited

U.S. PATENT DOCUMENTS 4,165,258  8/1979  Pye et al. .......................... 435/215

OTHER PUBLICATIONS

Wun et al., 1989, J. Biol. Chem. 264(14) 7862–7868.
Ye et al., 1987, J. Biol. Chem. 262:3718–3725.
Scoper, R. K., 1982, *Protein Purification*, Springer-Verlag, New York, pp. 126–321.
Ako et al., 1972, Biochem. Biophys. Res. Comm. 47: 1402–1407.
van Mourik et al., J. Biol. Chem. 259, 14914–14921 (1984).
Andreason et al., Ibid. 261, 7644–7651 (1986).
Nielsen et al., Thromb. Haemostas. 55, 206–212 (1986).
Kruithof et al., Blood 69, 460–466 (1987).
Kruithof et al., Ibid, 70, 1645–1653 (1987).
Wagner and Binder, J. Biol. Chem. 261, 14474–14481 (1986).
Sprengers et al., J. lab. Clin. Med. 105, 751–758 (1985).
Wun and Kretzmer, FEBS Lett. 210, 11–16 (1987).
Astedt et al., Fibrinolysis 1, 203–208 (1987).
Sprengers and Kluft, Blood 69, 381–387 (1987).
Kruithof, Fibrinolysis 2, 59–70 (1988).
Ishii et al., Meth. Enzymol. 91, 378–383 (1983).
Wun and Reich, J. Biol. Cjhem. 262, 3646–3653 (1987).

*Primary Examiner*—Margaret Moskowitz
*Assistant Examiner*—Keith C. Furman
*Attorney, Agent, or Firm*—Scott J. Meyer; James W. Williams, Jr.

[57] ABSTRACT

A method of purifying PAI-1 from a biological fluid source, e.g. conditioned media of Hep G2 or HT 1080 cells, containing PAI-1 is disclosed, which comprises subjecting the biological fluid to a modified urokinase affinity absorbent, e.g. anhydrourokinase ligand bound to a CNBr-activated agarose gel or urokinase mutated at amino acid position 356 from Ser to Gly and bound to the gel, and then eluting PAI-1 from said affinity absorbent. A method of stabilizing and/or activating PAI-1 is also disclosed, which comprises complexing PAI-1 with vitronectin.

12 Claims, 2 Drawing Sheets

AFFINITY PURIFICATION OF PLASMINOGEN ACTIVATOR INHIBITOR I USING A MODIFIED UROKINASE

CROSS-REFERENCE TO RELATED APPLICATION

This is a continuation-in-part of application Ser. No. 07/268,916, filed Nov. 9, 1988, now abandoned.

BACKGROUND OF THE INVENTION

The present invention relates to a novel method of purifying plasminogen activator inhibitor and, more particularly, to the use of a modified urokinase for the affinity purification of endothelial cell type plasminogen activator inhibitor.

The serine proteases urinary plasminogen activator (uPA) and tissue plasminogen activator (tPA) convert the zymogen plasminogen into active enzyme plasmin. This enzyme system has been implicated in various physiological and pathological processes including fibrinolysis, inflammation, tissue remodeling, ovulation, trophoblast implantation, tumor invasion and metastasis. A regulatory system exists which controls the conversion of plasminogen to plasmin by inhibiting the plasminogen activators (PAs). Several such inhibitors have been recognized: endothelial cell type PA inhibitor (PAI-1), placental type PA inhibitor (PAI-2), urinary PA inhibitor (PAI-3) and protease nexin.

PAI-1 appears to be the most efficient inhibitor of uPA and tPA among the known PAIs. The second order rate constants have been estimated to be on the order of $10^4$–$10^7$ $M^{-1}.S^{-1}$. PAI-1 has been found in plasma, platelet, placenta, and a variety of cell cultures. Three forms of PAI-1 have been recognized: (a) an active form; (b) a latent form that can be partially reactivated by treatment with sodium dodecyl sulfate (SDS), guanidinium hydrochloride, urea or phospholipid; and (c) a proteolytically degraded form which can not be reactivated.

PAI-1 was first purified from the conditioned medium of bovine aortic endothelial cell culture by a combination of concanavalin A-Sepharose ® chromatography and SDS-gel electrophoresis, as reported by van Mourik et al., *J. Biol. Chem.* 259 (23), 14914–14921 (1984). Subsequently, PAI-1 was also isolated from the conditioned media of human fibrosarcoma cell line HT 1080 [Andreasen et al., *J. Biol. Chem.* 261, 7644–7651 (1986); Nielsen et al., *Thromb. Haemostas.* 55, 206–212(1986); Kruithof et al., *Blood* 69(2), 460–466 (1987); *Ibid.* 70(5), 1645–1653 (1987)], HTC rat hepatoma [Zaheb et al., *Thromb. Haemostasis* 58, 1017–1023 (1987)], and human endothelial cells [Booth et al., *Eur. J. Biochem.* 165, 595–600 (1987)]. The isolated PAI-1s consistently show very low specific activity even after denaturant activation [1 μg PAI-1 inhibits 2–5 units (20–50 ng) of urokinase]. This suggests that less than 5% of the molecule was active if it is assumed that the inhibitor forms a 1:1 complex with uPA or tPA. An attempt was made to purify active PAI-1 from a human melanoma cell line, MJZJ, as described by Wagner and Binder, *J. Biol. Chem.* 261, 14474–14481 (1986). The final product was reported to have a specific activity of 62,000 International Units/mg in the inhibition of tPA which was still ten fold less than expected for fully active PAI-1 (~700,000 International Units/mg).

PAI-1 also is known to be produced by the human hepatoma cell line Hep G2 [Sprengers et al., *J. Lab. Clin. Med.* 105, 751–758 (1985); Wun and Kretzmer, *FEBS Lett.* 210, 11–16 (1987)].

Further background information on plasminogen activator inhibitors, including PAI-1, can be had by reference to recent reviews on the subject matter such as, for example:

Astedt et al., *Fibrinolysis* 1, 203–208 (1987); Sprengers and Kluft, *Blood* 69, 381–387 (1987); and Kruithof, *Fibrinolysis* 2, 59–70 (1988).

BRIEF DESCRIPTION OF THE INVENTION

In accordance with the present invention a novel method for purifying active PAI-1 from biological fluid sources is provided. The method comprises subjecting a biological fluid containing PAI-1 to a modified urokinase affinity adsorbent and then eluting PAI-1 from said affinity adsorbent. This method involves the use of an active site modified urokinase which reversibly binds the active PAI-1.

A preferred active site modified urokinase is obtained by reacting urokinase with phenylmethylsulfonyl fluoride followed by alkali treatment. The resulting product, hereinafter referred to an anhydrourokinase, was found to reversibly bind the PAI-1 when immobilized on a matrix of chromatographic bed material. A preferred matrix or coupling gel for immobilizing the anhydrourokinase ligand is a cyanogen bromide-activated agarose gel such as CNBr-activated SEPHAROSE 4B, which is commercially available from Pharmacia.

The end product of the urokinase modification reaction is essentially catalytically inactive; and when the modified protein is attached to CNBr-SEPHAROSE 4B, specifically binds PAI-1 in a reversible manner. These properties are in contrast to the native urokinase which is enzymatically active and forms covalent complexes with PAIs that are resistant to dissociation in sodium dodecyl sulfate (SDS), acidic pH, or other denaturing conditions.

The immobilized anhydrourokinase is highly specific in binding functionally active free PAI-1 or PAI-1: vitronectin complex. The proteins eluted from the anhydrourokinase-SEPHAROSE 4B column consist of substantially pure PAI-1 and/or vitronectin. Elution can be conveniently carried out with an acidified arginine solution, for example, by use of about 1M arginine/HCl at about pH 5.5.

Other suitable modified urokinases for use in the method of the invention can be made by mutation at the active site. For example, mutations can be made at the serine protease catalytic site residues His, Asp and Ser at amino acid positions 204, 255 and 356, respectively, of the 411 amino acid mature u-PA described by Holmes et al., *Bio/Technology* 3, 923–929 (1985). Illustrative of such mutations at these sites are His→Asn or Gln; Asp→Asn; and/or Ser→Gly or Cys. A preferred such mutation is Ser356→Gly.

The isolation of PAI-1 from biological fluids is illustrated herein in detail by purification from cell culture conditioned media of HT-1080 fibrosarcoma cells and, preferably, Hep G2 cells, although other cell sources of PAI-1 can similarly be used.

HEP G2 is a well-known and widely available human hepatoma cell line whose establishment and characteristics are described in U.S. Pat. No. 4,393,133. Samples of this cell line also are available to the public from the permanent collection of The American Type Culture Collection, Rockville, Md., under accession number ATCC HB 8065.

Likewise, HT-1080 is a well-known and widely available human fibrosarcoma cell line described by Rasheed et al., Cancer 33, 1027–1033 (1974). Cultures of this cell line are available to the public from the ATCC under accession number ATCC CCL 121.

These and other such PAI-1-producing cells can be grown at about 37° in conventional nutrient culture medium to express PAI-1. Suitable commercially available culture media are those described, for example, by Helen J. Morton, *In Vitro* 6(2), 89–108 (1970). These nutrient culture media contain amino acids, minerals, carbohydrates, vitamins and are frequently fortified with mammalian sera, e.g. fetal bovine sera or calf sera, and various growth factors. As used herein, the cells are preferably first grown in sera-containing medium and then transferred to sera-free medium supplemented with suitable growth factors such as lactalbumin hydrolysate, liver cell growth factor and the like.

The culture lysates and conditioned media of recombinant DNA organisms and cells that produce PAI-1 are other examples of biological fluid sources for application of the method of purifying PAI-1 in accordance with the present invention. This is illustrated, e.g., by the recombinant DNA *E. coli* expression of PAI-1 as described by Wun and Kretzmer, *FEBS. Lett.* 210, 11–16 (1987). Other suitable recombinant DNA sources of PAI-1 are illustrated by Ny et al., *Proc. Natl. Acad. Sci. USA* 83, 6776–6780 (1986); Andreason et al., *FEBS Lett.* 209, 213–218 (1986); Pannekoek et al., *EMBO J.* 5, 2539–2544 (1986); and Ginsburg et al., *J. Clin. Invest.* 78, 1673–1680 (1986).

In accordance with the method of the invention, a fully active PAI-1 together with an adhesive protein vitronectin or its fragment have been copurified from Hep G2 conditioned medium. PAI-1 has also been isolated from HT 1080 cultures using an essentially identical procedure. In the latter case, the isolated PAI-1 did not contain detectable amounts of vitronectin or other contaminant protein and the PAI-1 was only partially active. The results show that vitronectin binds, stabilizes and activates the PAI-1. Formation of complexes by mixing these two materials, preferably in about an equimolar ratio or with a small excess (e.g. about $1-1.1\times$ the stoichiometric amount) of the vitronectin, is useful for such purpose.

DETAILED DESCRIPTION OF THE INVENTION

Figure 1:
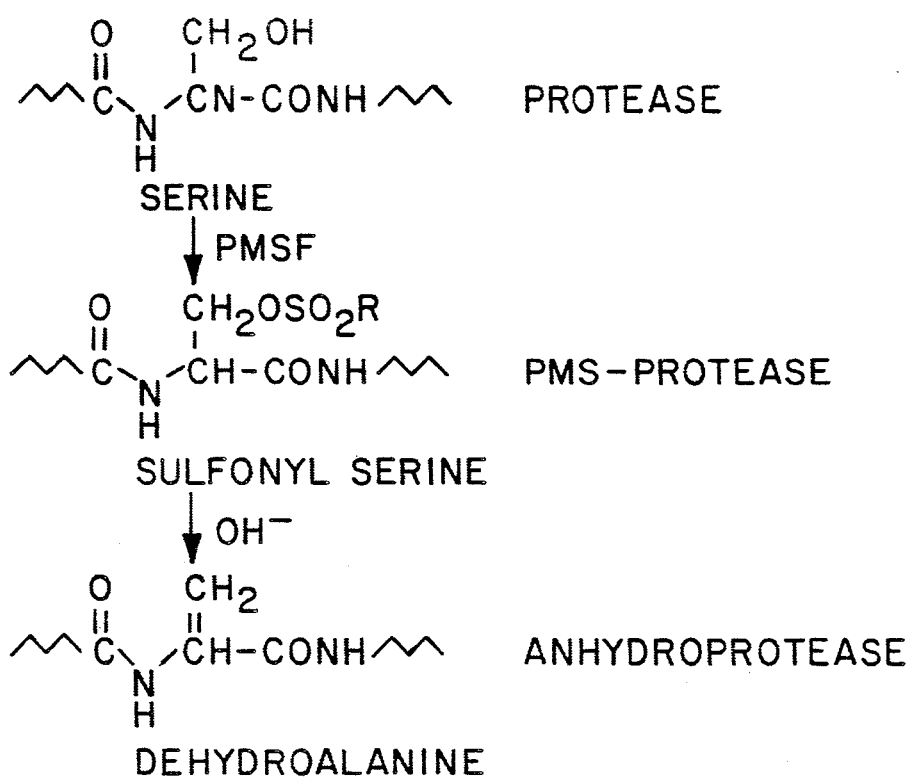

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which:

FIG. 1 shows partial chemical structures illustrating the conversion of serine proteases to anhydroproteases by reaction with phenylmethylsulfonyl fluoride (PMSF) followed by treatment with alkali (OH−).

Figure 2:
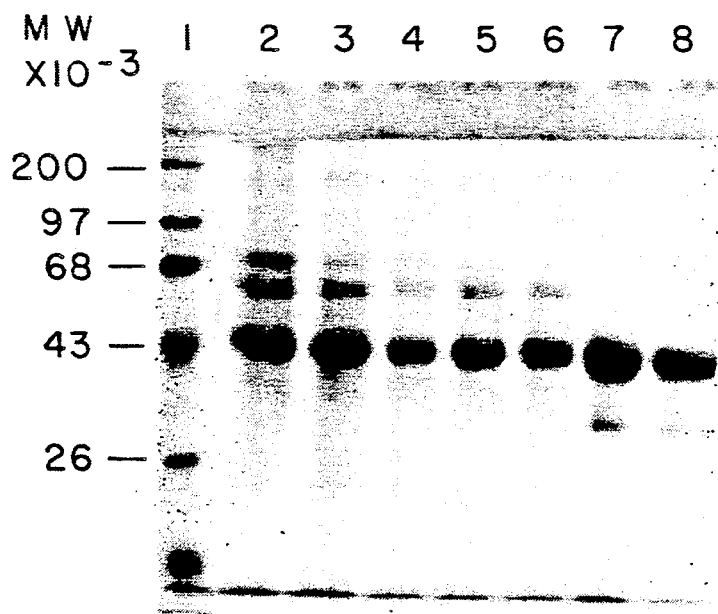

FIG. 2 shows the SDS-PAGE of the Hep G2 proteins eluted from an anhydrourokinase-SEPHAROSE 4B column. SDS-PAGE was carried out on a 10% polyacrylamide gel. The gel was stained with Coomassie Blue. Lane 1 is the molecular weight marker (MW$\times 10^{-3}$) Lanes 2-8 are Hep G2 PAI preparations 1 to 7, as described hereinafter.

Figure 3:
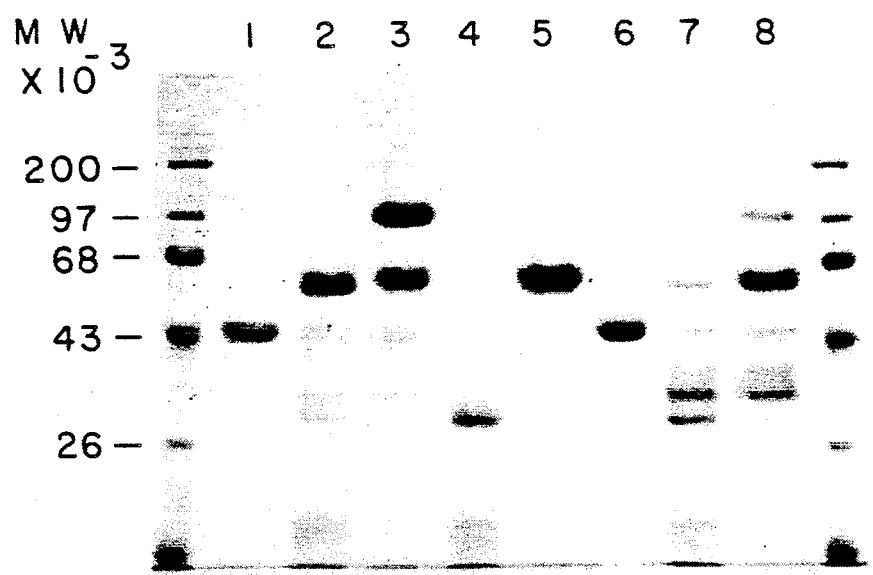

FIG. 3 shows the SDS-PAGE analysis of the interaction of PAI-1 with uPA and tPA. PAI-1, uPA or tPA alone and their mixtures were incubated at room temperature for 30 min. Sample buffer was added to the samples such that the final concentration of dithiothreitol was 20 mM. Electrophoresis was carried out on a gel containing 10% acrylamide. The gel was stained with Coomassie Blue. Lane 1, Hep G2 PAI-1, (1.8 µg); lane 2 Hep G2 PAI-1 (1.8 µg)+uPA (3.3 µg); lane 3, Hep G2 PAI-1 (1.8 µg)+tPA (3.5 µg); lane 4, uPA (3.3 µg); lane 5, tPA (3.5 µg); lane 6, HT 1080 PAI-1 (2.4 µg); lane 7, HT 1080 PAI-1 (2.4 µg)+uPA (3.3 µg); lane 8, HT 1080 PAI-1 (2.4 µg)+tPA (3.5 µg). The Hep G2 PAI-1 was stored in 1M arginine/HCl, pH 5.5, and has a specific activity of 105,000 P.I.U./A280 units. The HT 1080 PAI-1 was stored in 0.3M NH$_4$HCO$_3$ and has a specific activity of 5500 P.1.U./A280. Molecular weight marker lanes are shown at both sides of FIG. 3.

Figure 4:
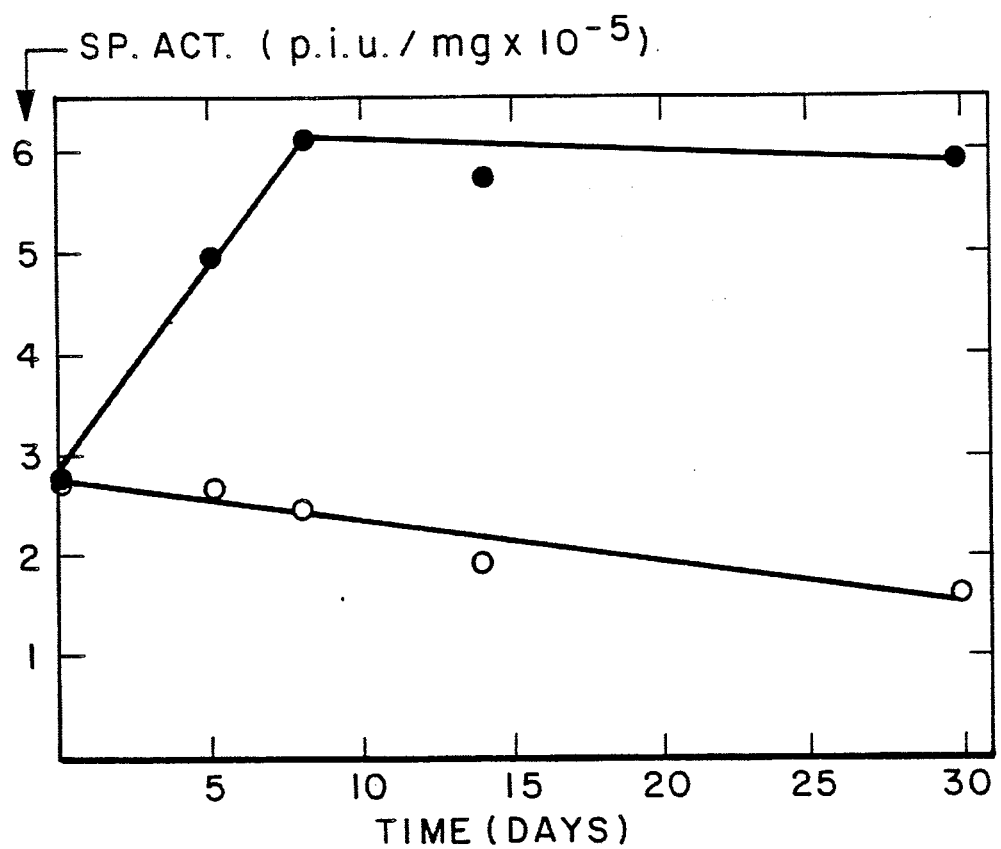

FIG. 4 is a graphical representation which shows the activation of PAI-1 by vitronectin. Purified HT 1080 PAI-1 (A280=0.7, in 1M Arginine/HCl, pH 5.5) was diluted 20 fold with PBB solution (PBS containing 5 mg/ml bovine serum albumin and 2.5 mg/ml bovine gamma globulin). The diluted PAI-1 was mixed with 1/10 volume of 500 µg/ml vitronectin dissolved in 50 mM NH$_4$HCO$_3$ or 50 mM NH$_4$HCO$_3$ alone. The mixtures were incubated at 4°. At indicated time points (shown as days) aliquots were taken and diluted with PBB solution for assay of PAI activity. PAI activity was measured by determining the inhibition of uPA activity using an amidolytic assay as described hereinafter. Specific activity (sp. act.) was calculated based on the PAI activity and the amount of PAI-1. The amount of PAI-1 was estimated from the absorbance at 280 nm, assuming A280 nm=1.0 for a protein concentration of 1 mg/ml. (●), + vitronectin; (0)-vitronectin.

The following detailed examples will further illustrate the invention although it will be appreciated that the invention is not limited to these specific examples.

EXAMPLE 1

Materials

Pure urokinase, (WINKINASE, uPA) was obtained from Winthrop Laboratories. Single chain tPA and aprotinin were purchased from American Diagnostica, Inc. The chromogenic substrate, L-pyroglutamyl-glycyl-L-arginine-P-nitroanilide (S-2444), was obtained from Helena Laboratories. Diisopropylfluorophosphate (ipr$_2$PF), dexamethasone, phenylmethylsulfonylfluoride (PMSF), phorbol 12-myristate 13-acetate (PMA), and lactalbumin hydrolysate were from Sigma. Liver cell growth factor (glycyl-histidinyl-lysine) and ITS premix (insulin-transferrin-selenium) were from Collaborative Research. Cyanogen bromide (CNBr) activated SEPHAROSE 4B (bead-formed, agarose gel, 45-165 µm) was from Pharmacia. Vitronectin was purchased from Calbiochem. Hep G2 hepatoma and HT 1080 fibrosarcoma cells were obtained from the American Type Culture Collection.

METHODS

Preparation of Anhydrourokinase-SEPHAROSE 4B

It is known that the active site serine residue of trypsin can be specifically converted to dehydroalanine by sequential treatment of trypsin with phenylmethylsulfonylfluoride (PMSF) and alkali [Ishii et al., *Meth. Enzymol.* 91, 378–383 (1983)]. The resulting modified protein, named anhydrotrypsin, is catalytically inactive but retains the ability to bind a variety of trypsin inhibitors. In a similar manner, the serine protease urokinase was converted to the corresponding anhydroprotease. FIG. 1 illustrates the reactions described above. To synthesize anhydrourokinase, modification reactions were carried out as follows: $1.0 \times 10^6$ CTA units of urokinase (Winkinase) were dissolved in 10 ml of a buffer containing 50 mM sodium phosphate, pH 7.4. To this solution was added 0.1 ml of 0.2M PMSF dissolved in acetone. The mixture was stirred for 15 min. at room temperature. Subsequently, 0.1 ml of 0.2M PMSF and 1 ml of 0.5M sodium phosphate, pH 7.4, were added and the solution was stirred for another 2.5 h. By amidolytic assay using the synthetic substrate, S-2444, it was found that over 99% of urokinase activity was inhibited. The solution was then dialyzed against 1 mM HCl/0.15M NaCl using Spectrapore #2 membrane at 4° C. for 3.5 h. After dialysis, the solution was chilled on ice. Ice cold 1M KOH (1.1 ml) was added and the mixture was incubated on ice for 20 min. The solution was then neutralized by adding 2.2 ml of 0.5M $NaH_2PO_4$, and 2.2 ml of 0.5M sodium phosphate, pH 7.4. To inactivate residual active urokinase, diisopropylfluorophosphate was added to a concentration of 5 mM and the solution was stirred at room temperature for 2 h. and at 4° C. overnight. The solution was then dialyzed for 3 h against a buffer containing 0.2M $NaHCO_3$ and 0.5M NaCl and the proteins were coupled to 0.8 g of cyanogen bromide activated SEPHAROSE 4B using the manufacturer's published procedure.

Amidolytic Assay for Plasminogen Activator Inhibitor

Plasminogen activator inhibitor was measured by determining the inhibition of uPA activity using the synthetic substrate, S-2444, as described by Wun et al., *J. Biol. Chem.* 257, 3276–3283 (1982); Wun and Reich, *Ibid.*, 262, 3646–3653 (1987). In brief, the inhibitor solution was first mixed with 10 ul of a uPA preparation (WINKINASE, 2000 Committee on Thrombolytic Agents units/ml or 1360 Ploug units/ml) for 5 min at room temperature. Then, an assay buffer containing 0.1M Tris/HCl, pH 8.8, 0.5% Triton ® X-100 and substrate was added to yield a final volume of 0.25 ml and S-2444 concentration of 0.2 mM. The rate of absorbance change at 405 ($\Delta A_{405\ nm}$/min.) was measured. Leo standard uPA or WINKINASE were used as reference. It was found that one Committee on Thrombolytic Agents unit of Winkinase was equivalent to 0.68 Ploug units of Leo uPA in the S-2444 amidolytic assay. Inhibitory activities are defined either as Ploug (P.I.U.) or Committee on Thrombolytic Agents (C.I.U.) inhibitory units based on the activity in the standard uPA-S2444 assay.

Preparation of Cultures and Collection of PAI-Containing Conditioned Medium

The human hepatoma cell line, Hep G2, was cultured in T-150 flasks to confluency in Dulbecco's Modified Eagle's Medium (DMEM) supplemented with 10% fetal bovine serum at 37° C. in a 5% $CO_2$ incubator. For large scale culture, 8 confluent T-150 flasks were trypsinized to seed each 10-chamber cell factory (6000-cm²). The cells were grown in DMEM supplemented with 10% fetal bovine serum for 1 week. To prepare the serum free conditioned medium, the cells were washed with phosphate buffered saline (PBS) and incubated in 1 liter of DLAGIP medium (DMEM supplemented with 0.5% lactalbumin hydrolysate, 50 U/ml aprotinin, 20 ng/ml liver cell growth factor, 1 X ITS-premix, and 100 ng/ml PMA). The serum free conditioned medium was collected and replaced with fresh medium every 2–3 days. The cells were kept in the above serum-free medium for more than 2 months.

The human fibrosarcoma cell, HT 1080, was cultured and expanded in DMEM supplemented with 10% fetal bovine serum as described above for Hep G2 cell. For collection of serum free medium, the cells were incubated in DMEM supplemented with 0.5% lactalbumin hydrolysate, 50 units/ml aprotinin and $1 \times 10^{-6}$M dexamethasone. The serum free medium was replaced once every 2–3 days. The cells were kept in the above serum-free medium for more than a month.

Electrophoretic Procedures

Analytical SDS-PAGE was performed according to the method of Laemmli, *Nature* 227, 680–685 (1970), using slab gel plates. The separating and stacking gels contain 10% and 4% acrylamide, respectively.

Amino Acid Sequence Analysis

Automated Edman degradation chemistry was used to determine the $NH_2$-terminal protein sequence. An Applied Biosystem, Inc., model 470A gas phase sequencer (Foster City, Calif.) was employed for the degradations [Hunkapiller et al., *Meth. Enzymol.* 91, 399–413 (1983)]. The respective phenylthiohydanotoin (PTH)-amino acid derivatives were identified by reverse phase-HPLC analysis in an on-line fashion employing an Applied Biosystems, Inc., Model 120A PTH Analyzer fitted with a Brownlee 2.1 mm I.D. PTH-C18 column.

Affinity Purification of PAI-1 from Hep G2 and HT 1080 Conditioned Media

The Hep G2 conditioned medium (60 liters) was concentrated by ultrafiltration using a YM30 spiral membrane on a DC1L concentrator (Amicon) to 3 liters. The concentrate was precipitated by ammonium sulfate (75% saturation). The precipitate was dissolved in $H_2O$ and dialyzed against 0.5M $NH_4HCO_3$-1% TRITON X-100 (octoxynol). The concentrate was adjusted to 300 ml, centrifuged at 44,000 g for 1 h. and filtered through a 0.45$\mu$ membrane before chromatography. The fresh concentrate contained 1000 P.I.U./ml of PAI activity.

For the purification of PAI-1, the concentrate was chromatographed on a lysine-Sepharose 4B column (5–1.5 cm) followed by an anhydrourokinase-SEPHAROSE 4B column (5.5–1.5 cm) at a flow rate of approximately 0.5 ml/min. at 4° C. The lysine-SEPHAROSE 4B removes plasminogen and serves as a guard column. After the concentrate had flowed through the columns, the lysine-SEPHAROSE 4B column was detached and washed with 0.2M 6-aminohexanoic acid and PBS for reuse. The anhydrourokinase-SEPHAROSE 4B column was washed with 50 ml of 0.5M $NH_4HCO_3$-1% TRITON X-100 and 50 ml of PBS. The proteins bound to the anhydrourokinase-SEPHAROSE 4B column were eluted with 20 ml 1M arginine/HCl, pH 5.5, and concentrated by Centricon 30 (Amicon) to approximately 1 ml.

The HT 1080 conditioned medium (12 liters) was precipitated by ammonium sulfate (75% saturation). The precipitate was redissolved in 90 ml $H_2O$ and dialyzed against a solution containing 0.5M $NH_4HCO_3$-1%

TRITON X-100 at 4° C. The solution was cleared by centrifugation at 44,000 g for 1 h. The fresh concentrate contained 2453 P.I.U./ml of PAI activity. For purification of PAI-1, the HT 1080 concentrate was chromatographed on the lysine-Sepharose 4B and the anhydrourokinase-Sepharose 4B columns as described above.

RESULTS

Properties of the Hep G2 and HT 1080 Cultures and Conditioned Media

Using an amidolytic assay which measures the inhibition of uPA activity as described above, one can readily assess the amount of PAI activity present in the cell-conditioned media. A number of supplements have been tested to examine their effect on PAI activity in the Hep G2 cell culture. Two supplements, ITS-premix (insulin-transferrin-selenium, Collaborative Research Product) and PMA (phorbol-12-myristate 13-acetate), were each alone found to increase the PAI activity 2-3 fold. A combination of both consistently increased the PAI activity up to 5 fold in the serum free medium collected after 2-day incubation, compared to a simultaneous culture without these supplements. A typical Hep G2 serum free medium contained 13, 21, and 23 P.I.U./ml PAI activity on day 1, 2 and 3, respectively. The PAI activity in the medium was however somewhat variable in different batches of medium collections, ranging from 8-30 P.I.U./ml of PAI activity. The variability may be partly due to the lability of PAI-1 in the diluted condition.

Based on these tests, a serum free medium DLAGIP (DMEM supplemented with 0.3% lactalbumin hydrolysate, 50 units/ml aprotinin, 20 ng/ml liver cell growth factor, ITS-premix, and 100 ng/ml PMA) was devised for conditioning the cell. In this medium the PAI production was enhanced and the viability of the cell was sustained for more than 2 months.

The HT 1080 cells after being grown to confluency, can also be maintained in serum-free medium for months. When cells were maintained in DMEM supplemented with 0.5% lactalbumin hydrolysate and 50 units/ml aprotinin, they produced a large amount of pro-uPA together with a small amount of PAI. When the medium was supplemented with $1 \times 10^6$ dexamethasone, the production of pro-uPA was essentially totally turned off, and the PAI activity increased approximately 8.5 fold in the 2-day conditioned medium as compared to a simultaneous culture maintained without dexamethasone. The PAI activity in the medium reached a maximum (~90 P.I.U./ml) on day 2 but declined to 80 and 20 P.I.U./ml on day 3 and day 4, respectively, suggesting that PAI activity is rather unstable at 37° C.

The PAI activity in the Hep G2 and HT 1080 conditioned media decays upon storage, being faster at 37° C. and slower at lower temperature. In order to preserve as much as possible of functionally active PAI-1 for purification, the volume of the media was quickly reduced by ultrafiltration and $(NH_4)_2SO_4$ precipitation for fast chromatography. The freshly prepared Hep G2 concentrate contained approximately 1000 P.I.U./ml of PAI activity and the activity was rather stable when stored at 4° C. in the concentrated state. A sample of Hep G2 concentrate stored at 4° C. for 6 months still preserved ~50% of PAI activity of the fresh concentrate. Unlike the stability of Hep G2 concentrate, the PAI activity in the HT 1080 concentrate was more labile. A fresh HT 1080 concentrate contained 2500 P.I.U./ml of PAI activity. The PAI activity decayed by 71% at 4° C. in 3 days and was essentially devoid of PAI activity by day 10. The difference in the PAI stability in the Hep G2 and HT 1080 concentrates may be partly due to the presence of a PAI-1 binding protein in the Hep G2 medium and its absence in the HT 1080 medium (see below).

Purification of Active PAI from Concentrated Media

It is known that PAIs form complexes with uPA and tPA which are not dissociated by SDS, suggesting that the complexes are formed by ester-like bonds involving the hydroxyl of serine at the active site of proteases and a carboxyl group in the inhibitor [van Mourik et al., *J. Biol. Chem.* 259, 14914-14921 (1984), Wun and Reich, *Ibid.* 262, 3646-3653 (1987)]. To dissociate the complexes, harsh conditions are required which may irreversibly denature PAIs. In order to preserve functionally active PAI, the active site serine of uPA was modified and the modified uPA was used as an affinity ligand to purify PAI. To modify the active site serine of uPA, a method was developed analogous to the method described for converting the serine protease trypsin to anhydrotrypsin by Ishii et al., supra. As illustrated in FIG. 1, the reactions involve the treatment of serine proteases with a synthetic inhibitor, phenylmethylsulfonylfluoride (PMSF), to form a phenyl-methylsulfonyl-protease and the subsequent conversion of the latter to anhydroprotease by alkali. The resulting anhydrourokinase was coupled to cyanogen bromide activated SEPHAROSE 4B.

The anhydrourokinase-SEPHAROSE 4B (~7ml gel bed) obtained by modifying $2 \times 10^6$ CTA units (~15 mg) of urokinase has a capacity to bind approximately $1.5 \times 10^5$ P.I.U. (~1.5 mg) of PAI-1. The Hep G2 concentrate (300 ml, 1000 P.1.U./ml) was passed through the column. The column was washed, the bound proteins were eluted and the column was reequilibrated with starting buffer as described above. Since the original Hep G2 concentrate contained approximately twice as much active PAI than the capacity of the column, the flow through fraction was rechromatographed on the reequilibrated anhydrourokinase column once more to deplete the majority of active PAI. Immediately after the second chromatography, the flow through pool contained 50 P.I.U./ml of PAI activity, indicating that 95% of active PAI was depleted by 2-time chromatography. The flow through fraction was allowed to stand at 4° C. for 2 days, the PAI activity was retested and it was unexpectedly found that the PAI activity spontaneously increased almost 3 fold (140 P.I.U./ml). Because of the apparent spontaneous activation of latent PAI, the flow through fractions were rechromatographed on anhydrourokinase-SEPHAROSE 4B a third time. The flow through fraction again showed spontaneous activation upon storage, being 33 P.I.U./ml at 2 hours after chromatography and 367 P.I.U./ml after storage for 10 days at 4° C. A total of 9 preparations of PAI were obtained by repeating the chromatography and storage over a period of 6 months and the flow through fraction of the last chromatography still showed spontaneous increase in PAI activity. The total amount of PAI-1 obtained in the 9 preparations was ~600,000 P.I.U. PAI was also isolated from HT 1080 medium concentrate by chromatography or anhydrourokinase-SEPHAROSE 4B as described above. Unlike the column flow-through fraction of Hep G2 which shows spontaneous regeneration of PAI activity, that of HT 1080 showed rapid decay of PAI activity, with 70% loss of activity after 3-day storage at 4° C.

The protein profiles of the preparations of Hep G2 PAI-1 are analyzed by SDS-polyacrylamide gel electrophoresis as shown in FIG. 2. All the preparations contained a major band with an apparent molecular weight of around 50 kDa. The earlier preparations also contained bands of 65 and 75 kDa under reducing conditions which were not present in the later ones. In addition, lower molecular weight proteins existed which migrated to the dye front in 10% polyacrylamide gel. When electrophoresis was carried out in higher polyacrylamide gel (17%), faintly stained fuzzy bands of molecular weights <15 kDa were present (data not shown). In contrast to the multiple bands of proteins isolated from Hep G2 concentrate, the HT 1080 protein isolated using essentially identical chromatographic methods consisted of a single 50 kDa protein (see FIG. 3, lane 5).

In order to further characterize these proteins, amino terminal sequence analysis was performed. The results are shown in Table I, below. The HT 1080 preparation, which showed only a 50 kDa band in SDS-PAGE was found to contain a single sequence with a heterogenous amino terminus. The preparation consisted of two alternative starting sequences which differed by a two amino acid extension at the amino terminus of one of the sequences. The two alternative starting sequences have a percent molar ratio of 63 to 37. These sequences exactly match the cDNA-derived sequences for PAI-1 [Wun and Kretzmer, FEBS Lett. 210, 11–16 (1987)]. The 50 kDa and 65+75 kDa bands of Hep G2 preparation 1 were gel purified by electro-elution and sequenced separately. The 50 kDa band contained the same PAI-1 amino terminal sequence with a percent molar ratio of 78 to 22 for the two alternative starting sequences. The 65 +75 kDa bands both contained a single amino terminal sequence which was identical to a known plasma protein, vitronectin. As mentioned above, preparation 7 of Hep G2 showed a major band of 50 kDa and some small proteins which migrated with the dye front, but there was no stainable band at 65-75 kDa region. When preparation 7 was sequenced directly, the sequence observed consisted of the amino termini of PAI-1 and vitronectin at close to an equimolar ratio (45:54). The above results indicate that PAI-1 and vitronectin or its fragments are copurified from Hep G2 medium by anhydrourokinase-Sepharose 4B.

TABLE I

Amino-terminal sequence of anhydrourokinase-SEPHAROSE 4 B purified proteins.

| Sample | Sequences Observed | %[a] |
|---|---|---|
| HT 1080 prep. | VHHPPSYVAHLASDFGVRVF | 63 |
|  | SAVHHPPSYVAHLASDFG | 37 |
| Hep G2 prep. 1. | VHHPPSYVAHLA | 78 |
| 50 kDa band | SAVHHPPSYVAH | 22 |
| 65 and 78 kDa bands[b] | DQES(C)KGR(C)TEGFNV | 100 |
| Hep G2 prep. 7 | VHHPPSYVAHLASDFGV | 26 |
|  | SAVHHPPSYVAH | 20 |
|  | DQES(C)KGR(C)TEGFNVDK | 54 |

[a]Values represent the percent molar ratio based on initial yields calculated by linear regression.
[b]The sample of Hep G2 preparation 1 was electro-phoresed in 10% SDS-PAGE. The gel was lightly stained and the bands were cut out with a blade and electro-eluted for amino acid sequence analysis.

An attempt was made to separate the 50 kDa PAI-1 from the 65-75 kDa vitronectin of Hep G2 preparation 1 by SUPEROSE 12 (cross-linked agarose beads, 30 μm) gel filtration on an FPLC system (Pharmacia). It was found that a large portion of PAI-1 coeluted with vitronectin right after the void volume (data not shown), suggesting that PAI-1 is tightly associated with vitronectin. The binding persists in physiological salt solution, such as phosphate buffered saline (PBS); in high ionic strength solution with nonionic detergent, such as PBS supplemented with 0.4 NaCl and 0.01% TWEEN 80 (polysorbate 80); and in a non-physiological buffer, such as 1M arginine/HCl, pH 5.5.

Specific Activity and Stability of Purified PAI-1

Because of the copurification of decreasing amounts of intact vitronectin with PAI-1 in successive chromatographic purifications of Hep G2 medium on an anhydrourokinase-SEPHAROSE 4B column, the consecutive preparations of PAI-1 showed a steady increase of specific activity. In the later preparations (prep. 6, 7, 8, and 9), the specific activity reached a maximum of 102,000±15,600 P.I.U./A280 unit. Assuming that the contribution of vitronectin fragment to the absorbance at 280 nm in these preparations is small compared with PAI-1, this specific activity is close to what would be obtained from a fully active PAI-1. The Hep G2 PAI-1 stored at high concentration (A280>0.9) in 1M arginine at 4° C. or −70° C. appeared to be stable. The specific activity did not decrease upon freezing and thawing a dozen times during a 2-year period. When the inhibitor was dialyzed against phosphate buffered saline, the specific activity declined to approximately 30,000 P.I.U./A280.

HT 1080 PAI-1 purified by anhydrourokinase-SEPHAROSE 4B had a specific activity of 23,700±6200 P.I.U./A280 when stored in 1M arginine/HCL, pH 5.5. This specific activity was only a quarter that of Hep G2 PAI-1, despite the fact that the isolation method and storage conditions were identical. The specific activity dropped to approximately 5500 P.I.U./A280 after dialysis against PBS or 0.3M NH4HCO3 and declined further upon storage in these buffers.

SDS-PAGE Analysis of the Interaction of PAI-1 with uPA and tPA

The ability of the purified PAI-1s to form complexes with uPA and tPA was studied by SDS-PAGE analysis. A high activity Hep G2 PAI-1 preparation (specific activity 102,000 P.I.U./A280) and a low activity HT 1080 PAI-1 (specific activity 5500 P.I.U./A280) were incubated with uPA and tPA and analyzed on SDS-PAGE. The results are shown in FIG. 3. When the Hep G2 PAI-1 was incubated with excess uPA or tPA, the PAI-1 band essentially disappeared and new bands of complexes with molecular weights of 56 kDa and 95 kDa (lanes 2 and 3) were formed. These data strongly indicate that the isolated Hep G2 PAI-1 was indeed fully active. On the contrary, when a low activity HT 1080 PAI-1 was incubated with an excess of uPA or tPA, there were extensive degradations with formation of only small amounts of the 56 kDa and 95 kDa complexes (lanes 7 and 8)

Activation of PAI-1 by Vitronectin

The above tests show that purified HT 1080 PAI-1 is not fully active in contrast to Hep G2 PAI-1 which contained copurified vitronection or its fragment and is essentially fully active. In view of these results, the effect of vitronection on the PAI-1 activity was examined. A purified HT 1080 PAI-1 preparation which has a specific activity of 28,300 P.1.U./mg protein was incubated with or without 50 μg/ml of vitronection in the presence of 50 mM L-arginine and the carrier proteins, bovine serum albumin and bovine gamma globulin at 4° C. It was found that the PAI-1 activity slowly decreased from 28,300 to 16,100 P.I.U./mg in the absence of vitronection over a 30 day incubation period. In the presence of vitronectin, in contrast, the PAI-1 activity increased with time reaching a maximum of 61,200 P.1.U./mg after 8 days at 4° C. and the activity barely decreased during an additional 22-day incubation. These results strongly suggest that vitronectin is capable of activating latent PAI-1 and stabilizing the PAI-1 activity.

Stability of Purified PAI-1 to SDS-Treatment

It has been widely observed that cell-conditioned media contain mainly (>95%) latent PAI-1 and that SDS-treatment leads to enhanced PAI activity. See, e.g., van Mourik et al., supra. The SDS-effect on the PAI-1 preparations was investigated. Table II summarizes the results. Treatment of a fully active Hep G2 PAI-1 preparation with 0.2% SDS at room temperature for 15 min resulted in a decrease of PAI-1 activity to 34%. Similar treatment of a 19% active HT 1080 PAI-1 resulted in a small decrease of activity to the 14% level. In contrast, SDS-treatment of a 1.9% active HT 1080 PAI-1 caused a 2-fold increase in specific activity. These results suggest that SDS-treatment causes partial inactivation of fully or moderately active PAI-1, in contrast to largely latent PAI-1 which can be partially activated by SDS, as has been reported by others.

TABLE II

Stability of purified PAI-1 to SDS-treatment

| | Untreated[e] | | SDS-treated[d] | |
|---|---|---|---|---|
| | Activity (P.I.U./A280) | % Active[f] Molecule | Activity (P.I.U./A280) | % Active[f] Molecule |
| Hep G2 PAI-1[a] | 102,000 | 100 | 35,000 | 34 |
| HT 1080 PAI-1[b] | 19,700 | 19 | 14,600 | 14 |
| HT-1080 PAI-1[c] | 1,958 | 1.9 | 4,000 | 3.9 |

[a]Hep G2 PAI-1 was stored in 1M arginine/HCl, pH 5.5 ($A_{280}$ = 0.91).
[b]HT 1080 PAI-1 was stored in 1M arginine/HCl, pH 5.5 ($A_{280}$ = 0.70).
[c]HT 1080 PAI-1 was stored in 0.3M $NH_4HCO_3$ ($A_{280}$ = 0.80).
[d]Five μl of Hep G2 or HT 1080 PAI-1 was mixed with 5 μl of 0.4% SDS and retained a room temperature for 15 min. Subsequently 5 μl of 8% TRITON X100 was added and the mixture was diluted into trisbuffered saline containing 5 mg/ml BSA for PAI activity assays as described hereinbefore.
[e]This test was carried out as in c except that 5 μl of 0.4% SDS and 5 μl of 8% TRITON X100 were premixed before addition to the PAI-1 samples.
[f]Calculation based on the assumption that fully active molecule has a specific activity of 102,000 P.I.U./$A_{280}$.

EXAMPLE 2

Isolation of Active PAI-1 Using a Urokinase Variant with the Active Site Serine-356 Mutated into Glycine Assembly of a synthetic gene coding for human prourokinase A gene coding for human prourokinase (prouPA) was constructed from a 400-bp cDNA fragment and 900-bp of assembled synthetic oligonucleotides based on the cDNA sequence published by Holmes et al. [Bio/Technology 3, 923 (1985). The 400-bp cDNA fragment was isolated by screening a HT1080 fibrosarcoma lambda gt11 cDNA library with a rabbit antibody against human urokinase according to the method described by Young and Davis, Science 222, 778 (1983). The 900-bp of assembled DNA was divided into 5 discrete sub-assemblies of 170 to 240 bp synthesized using beta-cyanoethyl protected phosphoramidite on Applied Biosystems model 380 DNA synthesizer [Synah et al., Nucl. Acids Res. 12, 4539 (1984)]. The assembly and cloning of oligonucleotides into sequencing vectors were accomplished by 'shotgun' assembly using the method described by Gundstrom et al., Nucl. Acids Res. 13, 3305 (1985). In designing the synthetic oligonucleotide, base changes were made to include restriction sites for convenient construction, subcloning, and minimizing secondary structure within the oligonucleotide while maintaining the correct amino acid sequence.

Site-Specific Mutation of the Prourokinase Gene to Create a Prourokinase Mutant with the Active Site Serine-356 Converted into Glycine-356

To convert the serine-356 in the active site of prourokinase into glycine-356, the DNA coding for serine at this position was mutated from TCA into GGA using the Amersham oligonucleotide-directed in vitro mutagenesis system which is based on the method of Eckstein et al., Nucl. Acids Res. 14, 9679 (1986).

Expression of the Prourokinase Mutant, Pro-uPA G356

The prourokinase mutant with glycine-356 replacing the serine (pro-uPA G356) is expressed in the mouse C127 cell using a bovine papilloma virus (BPV) based vector, pMON1123. This vector consists of the entire BPV genome cloned in the pBR322 derivative pML2 and utilizes the mouse metallothionein 1 promoter and the SV40 Late poly A addition site to direct expression of proteins encoded by DNA fragments inserted into a unique BamHI site. For expression of the pro-uPA G356, pMON1123 and the DNA coding for the mutant were digested with BamHI and ligated to yield the plasmid pMON9357. Mouse C127 cells were grown and cotransfected with pMON9357 and pSV2neo by the method described by Ramabhadran et al., Proc. Nat'l. Acad. Sci. USA 81, 6701 (1984). Following selection with G418 (Geneticin antibiotic), resistant colonies were picked and seeded into wells of 24-well plates. Conditioned media from each well was then assayed for prourokinase antigen by enzyme linked immunosorbent assay. One high expression clone producing approximately 40 μg pro-uPA G356/$10^6$ cell/24 hr was chosen for scale up for isolation of the mutant protein.

Isolation of Recombinant C127 Urokinase Mutant uPA-G356

The pro-uPA G356 producing cell line was cultured in Dulbecco's Modified Eagle's Medium (DMEM) containing 10% fetal bovine serum. The cells were grown to confluency in 150-$cm^2$ flask. Each flask was trypsinized and used to seed one 850-$cm^2$ roller bottle. After confluency, the cells from each bottle were used to seed one 10-chamber cell factory (6000-$cn^2$). Upon reaching confluency, the cells were washed with phosphate buffered saline and incubated in a serum free DMEM. The serum free conditioned medium was collected every 2-day and replaced with fresh medium. The pooled medium (5 liter) was concentrated 10 fold using a Amicon YM30 membrane. Plasmin (4 CU, Kabi product) was added to the concentrate and the mixture was incubated at room temperature overnight to convert the pro-UPA G356 to uPA G356. Aprotinin (2000 KIU, Sigma product) was then added to stop the plasmin digestion. The concentrate was subjected to ammonium sulfate precipitation. Proteins precipitated between 30 and 90% saturation of ammonium sulfate were collected and dialyzed against a solution containing 50 mM Na-PO4, pH 7.5, 0.4M NaCl (Buffer A). The solution was clarified by centrifugation at 40,000 g for 1 h. The supernatant was chromatographed on a p-aminobenzamidine-agarose column (1.5×19 cm, Pierce product). The column was washed with five column volumes of Buffer A and eluted with a buffer containing 0.1M sodium acetate, pH 4, 0.4M NaCl. The eluted protein was concentrated and dialyzed against phosphate buffered saline. The purified uPA G356 was coupled to the cyanogen bromide activated Sepharose 4B at a ratio of about 5 mg protein/ml gel according to the procedure recommended by the manufacturer.

Isolation of Active PAI-1 by Affinity Chromatography on the uPA G356-SEPHAROSE 4B The methods for isolation of PAI-1 from the cell culture medium by chromatography on the uPA G356-SEPHAROSE 4B are identical to that described for the purification PAI-1 using anhydrourokinase-SEPHAROSE 4B in Example 1, above.

RESULTS

In the purification of active PAI-1, the chromatographic behavior of the uPA G356-Sepharose 4B is similar to that of the anhydrourokinase-SEPHAROSE 4B. Both yield active PAI-1 or PAI-1/vitronectin complex in essentially pure form.

| Abbreviated Designation | Amino Acid | |
| --- | --- | --- |
| A | Ala | Alanine |
| C | Cys | Cysteine |
| D | Asp | Aspartic Acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

What is claimed is:

1. A method of purifying PAI-1 from a biological fluid containing PAI-1 comprising contacting said biological fluid with a modified urokinase affinity adsorbent and then eluting PAI-1 from said affinity adsorbent with an acidified arginine solution, wherein said modified urokinase is selected from the group consisting of anhydrourokinase and urokinase mutated at amino acid position 356 from Ser to Gly.

2. The method of claim 1 in which the modified urokinase is anhydrourokinase.

3. The method of claim 1 in which the modified urokinase affinity adsorbent is anhydrourokinase ligand bound to a cyanogen bromide-activated agarose.

4. The method of claim 2 in which the biological fluid is the cell culture conditioned medium of Hep G2 cells.

5. The method of claim 2 in which the biological fluid is the cell culture conditioned medium of HT 1080 cells.

6. The method of claim 4 in which the modified urokinase affinity adsorbent is anhydrourokinase ligand bound to a cyanogen bromide-activated agarose.

7. The method of claim 5 in which the modified urokinase affinity adsorbent is anhydrourokinase ligand bound to a cyanogen bromide-activated agarose.

8. A method of purifying PAI-1 from a biological fluid containing PAI-1 comprising contacting said biological fluid with anhydrourokinase affinity adsorbent and then eluting PAI-1 from said anhydrourokinase affinity adsorbent with about 1M arginine/HCl at about pH 5.5.

9. The method of claim 8 in which the anhydrourokinase is bound to a cyanogen bromide-activated agarose and in which the biological fluid is the cell culture conditioned medium of Hep G2 cells.

10. The method of claim 8 in which the anhydrourokinase is bound to a cyanogen bromide-activated agarose and in which the biological fluid is the cell culture conditioned medium of HT 1080 cells.

11. The method of claim 1 in which the modified urokinase is urokinase mutated at amino acid position 356 from Ser to Gly.

12. The method of claim 11 in which the modified urokinase is bound to cyanogen bromide-activated agarose.

* * * * *